United States Patent
Suh

(10) Patent No.: US 8,894,688 B2
(45) Date of Patent: Nov. 25, 2014

(54) ADJUSTABLE ROD DEVICES AND METHODS OF USING THE SAME

(75) Inventor: Sean Suh, Plymouth Meeting, PA (US)

(73) Assignee: Globus Medical Inc., Audubon, PA (US)

( * ) Notice: Subject to any disclaimer, the term of this patent is extended or adjusted under 35 U.S.C. 154(b) by 140 days.

(21) Appl. No.: 13/283,118

(22) Filed: Oct. 27, 2011

(65) Prior Publication Data

US 2013/0110171 A1    May 2, 2013

(51) Int. Cl.
*A61B 17/70* (2006.01)

(52) U.S. Cl.
CPC ......... *A61B 17/7014* (2013.01); *A61B 17/7031* (2013.01); *A61B 17/7028* (2013.01)
USPC ............ 606/257; 606/254; 606/258; 606/259

(58) Field of Classification Search
USPC ................................. 606/254–259; 623/17.12
See application file for complete search history.

(56) References Cited

U.S. PATENT DOCUMENTS

| | | | |
|---|---|---|---|
| 2003/0055427 A1* | 3/2003 | Graf | 606/61 |
| 2005/0165396 A1* | 7/2005 | Fortin et al. | 606/61 |
| 2006/0189985 A1* | 8/2006 | Lewis | 606/61 |
| 2009/0234388 A1* | 9/2009 | Patterson et al. | 606/246 |
| 2010/0042152 A1* | 2/2010 | Semler et al. | 606/250 |

* cited by examiner

*Primary Examiner* — Eduardo C Robert
*Assistant Examiner* — Julianna N Harvey

(57) ABSTRACT

A medical device includes a first elongate member defining an interior region and configured to be coupled to a first anatomical structure within a body and a second elongate member configured to be coupled to a second anatomical structure within the body. A portion of the second elongate member is configured to be disposed within the interior region. The first and second elongate members collectively have a first configuration in which they collectively have a first length when the portion of the second elongate member is disposed within the interior region of the first elongate member. When coupled to the first and second anatomical structures, the first and second elongate members can be moved to a second configuration in which they collectively have a second length different than the first length.

19 Claims, 9 Drawing Sheets

US 8,894,688 B2

ADJUSTABLE ROD DEVICES AND METHODS OF USING THE SAME

TECHNICAL FIELD

This disclosure relates generally to medical devices and more particularly to adjustable rod devices configured to be coupled to a first portion of an anatomical structure and a second portion of an anatomical structure of a patient and adjusted to accommodate a changing size of the patient.

BACKGROUND

A variety of medical devices and medical device systems are implanted within a body of a patient to provide support or stabilization to a portion or portions of the patient's body. For example, some medical device systems are implanted and coupled to backbones or spines of patients and are configured to provide support to the spinal bone structure of the patient. Some medical device systems that are configured to provide support to the spinal bone structure of a patient include support members or rods that extend between various portions of the medical device system to help maintain a specific distance between such portions of the medical device system. For example, the support members or rods may extend between portions of the medical device system that are coupled to adjacent vertebra to maintain a specific distance between the portions of the medical device system (and the vertebra to which the portions of the medical device system are coupled).

In some cases, after implantation, the portion of the patient's body being supported or stabilized by the support members or rods of the medical devices or medical device systems may grow, for example, in the case of a young patient. It then may be necessary to perform an additional medical procedure to replace a portion of the medical device (e.g., the support members or rods) or the entire implanted medical device or medical device system Accordingly, there is a need for a support or rod device of an implantable medical device or medical device system that may be adjusted after implantation to accommodate changes in the size of the portion of the body being supported or stabilized.

SUMMARY

In one embodiment, a medical device includes a first elongate member defining an interior region and configured to be coupled to a first anatomical within a body of a patient. A second elongate member is configured to be coupled to a second anatomical structure within the body of the patient, and a portion of the second elongate member is configured to be disposed within the interior region of the first elongate member. The first elongate member and the second elongate member collectively have a first configuration in which the first elongate member and the second elongate member collectively have a first length when the portion of the second elongate member is disposed within the interior region of the first elongate member. When the first elongate member is coupled to the first anatomical structure and the second elongate member is coupled to the second anatomical structure, the first elongate member and the second elongate member are configured to be moved from the first configuration to a second configuration in which the first elongate member and the second elongate member collectively have a second length different than the first length.

In another embodiment, a medical device includes a first elongate member that defines an interior region and is configured to be coupled to a first anatomical structure within a body of a patient. A second elongate member is configured to be coupled to a second anatomical structure within the body of the patient and at least a portion of the second elongate member is movably disposed within the interior region of the first elongate member. The first elongate member and the second elongate member collectively have a first length when the first elongate member is coupled to the first anatomical structure and the second elongate member is coupled to the second anatomical structure. At least one of the first elongate member or the second elongate member is configured to move relative to other when a force is exerted by at least one of the first anatomical structure on the first elongate member or the second anatomical structure on the second elongate member such that the first elongate member and the second elongate member collectively have a second length different than the first length.

In yet another embodiment, a medical device includes a first elongate member defining an interior region and configured to be coupled to a first anatomical structure within a body of a patient. A second elongate member includes a threaded portion and is configured to be coupled to a second anatomical structure within the body of the patient. At least a portion of the threaded portion of the second elongate member is telescopically disposed within the interior region of the first elongate member. An adjustment member is coupled to the first elongate member and threadably coupled to the threaded portion of the second elongate member. The first elongate member and the second elongate member collectively have a first configuration in which the first elongate member and the second elongate member collectively have a first length. When the first elongate member is coupled to the first anatomical structure and the second elongate member is coupled to the second anatomical structure, the first elongate member and the second elongate member are configured to be moved from the first configuration to a second configuration when the adjustment member is actuated. The first elongate member and the second elongate member collectively have a second length different than the first length when in the second configuration.

In another embodiment, a method includes coupling a first elongate member to a first anatomical structure within a body of a patient and coupling a second elongate member to a second anatomical structure within the body of the patient. At least a portion of the second elongate member is disposed within an interior region defined by the first elongate member. The first elongate member and the second elongate member collectively have a first length when the first elongate member is coupled to the first anatomical structure and the second elongate member is coupled to the second anatomical structure. After the coupling the first elongate member and the coupling the second elongate member, moving the first elongate member relative to the second elongate member such that the first elongate member and the second elongate member collectively have a second length different than the first length.

DETAILED DESCRIPTION

The devices and methods described herein are generally directed to medical devices that can be used to support and/or stabilize anatomical structures within a body of a patient. In some embodiments, the devices and methods described herein are configured to provide support to a spine or back of a patient. In other embodiments, other portions of the body of the patient can be supported by the devices described herein.

In some embodiments, the medical devices described herein (also referred to as "apparatus" or "device") can be used with and coupled to portions of a medical device or system that is configured to provide support or stabilization to a portion of a patient's body, such as to a spine of the patient. For example, the medical devices described herein can be configured to be coupled to a first support member (not shown) and a second support member (not shown) of a spinal stabilization device or system. In some embodiments, the medical devices can be used as a support rod that extends between two anatomical structures within such a device or system.

The medical devices described herein can be implanted into a patient's body in a first configuration in which the medical device has a first length, and while coupled within the body, moved to a second configuration in which the medical device has a second length different than the first length. In other words, the medical devices described herein can be advantageously adjusted (such as elongated or shortened) while coupled within the body of a patient to accommodate a change in size of the body of the patient. For example, in the case of a young patient, the medical device can be adjusted or elongated as the patient's body grows. In some embodiments, a length of the medical device can automatically be adjusted while coupled within the body of the patient without performing a separate medical procedure. In some embodiments, a length of the medical device can be adjusted during a percutaneous procedure to access the medical device while coupled within the body of the patient.

FIGS. 1-5 illustrate an adjustable medical device 100 according to an embodiment. The medical device 100 includes a first elongate member 102 and a second elongate member 104, each of which can be coupled to an anatomical structure within a patient's body, such as, for example, via a support member (not shown) as mentioned above. For example, the first elongate member 102 can be coupled to a support member that is anchored to or otherwise coupled to a first vertebra within a spine of a patient, and the second elongate member 104 can be coupled to a second vertebra via a support member that is coupled to the second vertebra.

Figure 1:
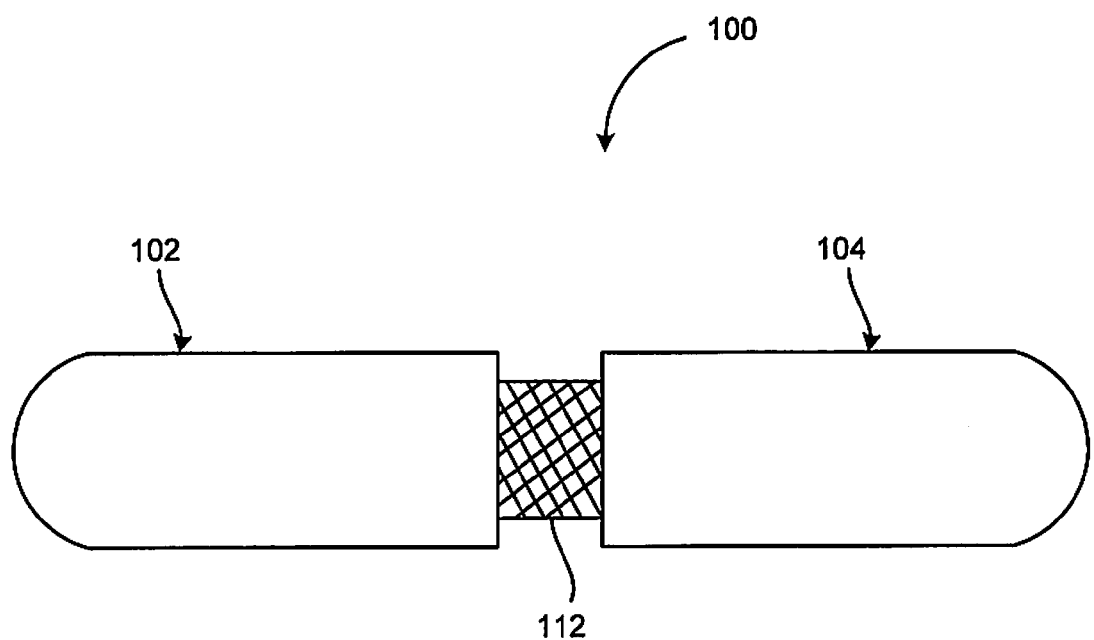
FIG. 1 is a side view of a medical device according to an embodiment of the invention.
Figure 2:
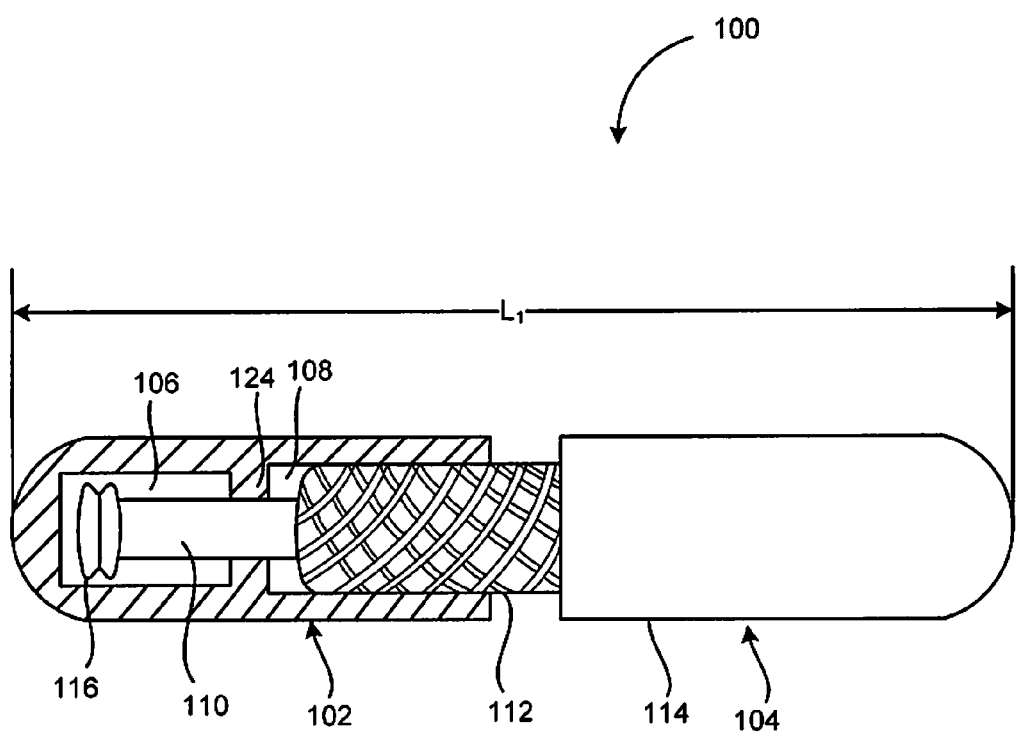
FIG. 2 is a side view partially in cross-section of the medical device of FIG. 1, shown in a first configuration.
Figure 3:
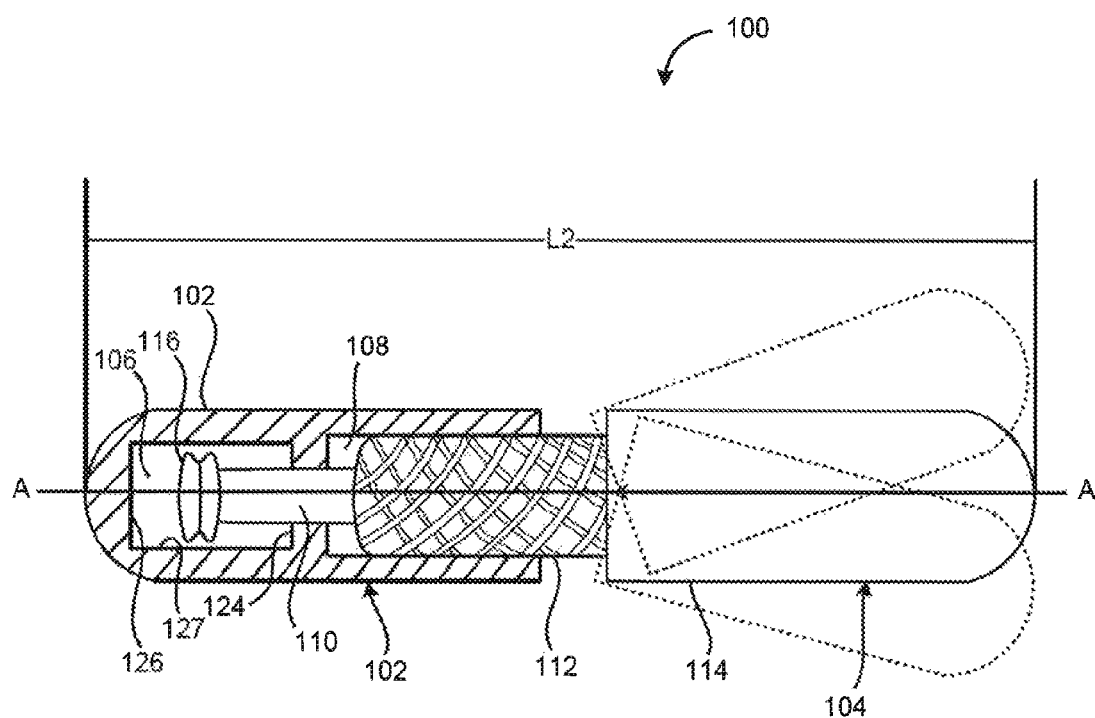
FIG. 3 is a side view partially in cross-section of the medical device of FIG. 1, shown in a second configuration.

As shown in FIGS. 2 and 3, the first elongate member 102 defines a first interior region 106 and a second interior region 108 separated by an annular wall 124 that defines an opening in fluid communication with the first interior region 106 and the second interior region 108. The first interior region 106 can contain therein a fluid as described in more detail below.

The second elongate member 104 includes a first portion 110, a second portion 112 and a third portion 114. The first portion 110 is movably disposed within the first interior region 106 and the second interior region 108 and extends through the opening defined in the annular wall 124. The annular wall 124 can help stabilize the first portion 110 as it is moved back and forth within the first interior region 106 and the second interior region 108. At least a portion of the second portion 112 of the second elongate member 104 is movably disposed within the second interior region 108. The third portion 114 of the second elongate member 104 can be coupled to an anatomical structure, such as, for example, via a support member, such as a pedicle screw, (not shown) as described above.

Figure 4:
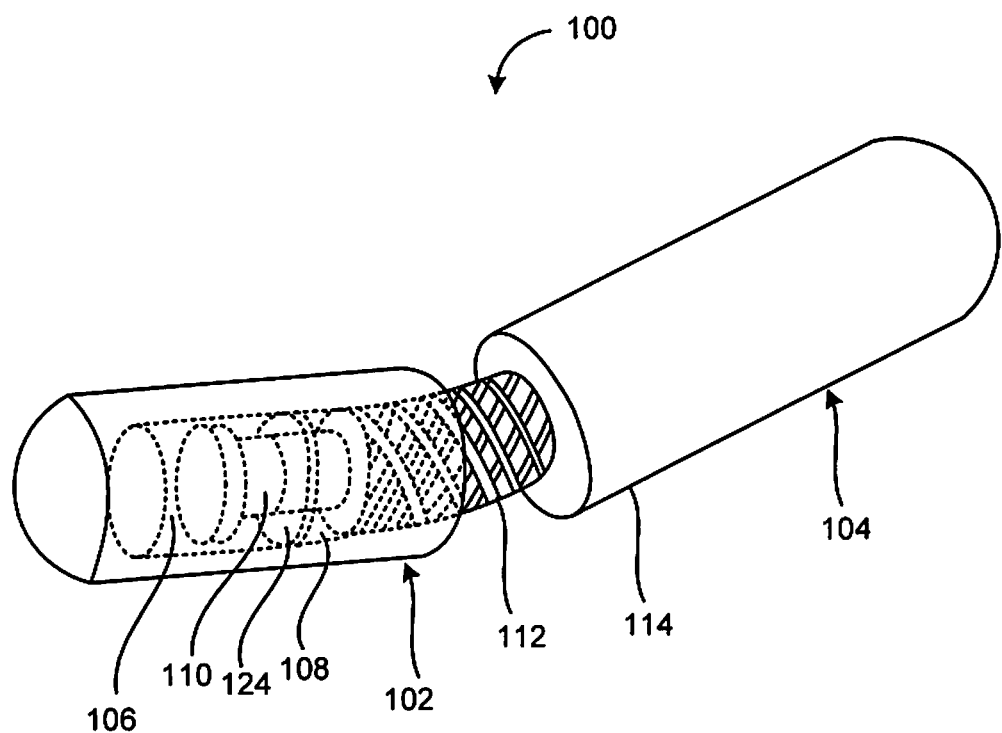
FIG. 4 is a perspective view of the medical device of FIG. 1 shown partially transparent and in the second configuration.

The second portion 112 of the second elongate member 104 can be formed with a flexible material such that it can provide flexible movement of at least a portion of the second elongate member 104. For example, as shown in dashed lines in FIG. 3, the second portion 112 of the second elongate member 104 can bend or flex at a variety of different angles relative to a longitudinal axis A-A defined by the first elongate member 102, such that the third portion 114 is disposed at different angles relative to the longitudinal axis A-A. FIG. 4 also shows the second portion 112 curved or bent an angle relative to the first elongate member 102 and the third portion 114 of the second elongate member 104 disposed at an angle relative to the first elongate member 102. The flexibility of the second portion 112 of the second elongate member 104 allows for increased maneuverability within a body of a patient during or post implantation, for example, implantation of the medical device 100 within the patient. In some embodiments, the second portion 112 can be formed with a flexible cable.

The medical device 100 can have a first configuration in which the medical device 100 has a first length $L_1$, as shown in FIG. 2, and while implanted within a patient's body can be moved to a second configuration in which the medical device 100 has a second length $L_2$, as shown in FIG. 3. For example, the first elongate member 102 can be coupled to a first anatomical structure (e.g., a first vertebra) and the second elongate member 104 can be coupled to a second anatomical structure (e.g., a second vertebra). When initially implanted, the medical device 100 can have a first length $L_1$ to accommodate the size/distance needed for the particular anatomical structures. Said another way, the first elongate member 102 and the second elongate member 104 (when coupled together) can collectively have a first length $L_1$. After implantation, the patient's body may change, and thus change the distance between the two anatomical structures of the patient. For example, a body of a young patient may grow after the medical device 100 has been implanted. In such a case, it may be desirable to adjust the length of the medical device 100 while it is implanted. In some embodiments, the medical device 100 can be used in motion preservation and/or structure stabilization procedures.

In this embodiment, the anatomical structures to which the medical device 100 is coupled can apply forces to the medical device 100 and cause the first elongate member 102 and the second elongate member 104 to move relative to each while implanted within the body. For example, the first portion 110 of the second elongate member 104 can slidably or telescopically move back and forth along the longitudinal axis A-A of the first elongate member 102 within the interior region 106 of the first elongate member 102. The first portion 110 can serve as a piston shaft that extends a piston head 116, as discussed in more detail below. Accordingly, the length $L_1$ of the medical device 100 can change before, during, or after implantation to a different length $L_2$. The length $L_2$ can be greater than the length $L_1$ (as shown in FIGS. 2 and 3) or less than the length $L_1$.

To control the rate of movement between the first elongate member 102 and the second elongate member 104 relative to each other and/or to control the force that is needed to move the first elongate member 102 and the second elongate member 104 relative to each other, the first interior region 106 of the first elongate member 102 can contain a volume of fluid (not shown) that can act against the forces being applied by the body. In some embodiments, the volume of fluid can delay the telescopic movement of the second elongate member 104 within the first interior region 106 and the second interior region 108. In some embodiments, the volume of fluid can maintain the second elongate member 104 at a desired position relative to the first elongate member 102.

The rate of delay and/or the force needed to move the second elongate member 104 relative to the first elongate member 102 can be varied depending on factors, such as, for example, the volume of fluid (e.g., the amount), the type of fluid and/or the viscosity of the fluid used and disposed within the first interior region 106. Thus, the viscosity, type and volume (e.g., amount) of the fluid can be varied to accommodate a particular desired rate of adjustment (e.g., elongation or shortening) of the medical device 100. In some embodiments, the fluid can be, for example, air.

In some embodiments, a volume of fluid is disposed in the first interior region 106 between the piston head 116 and an end wall 126 (see, e.g., FIG. 3) of the first elongate member 102. The piston head 116 can be sized (e.g., have an outer diameter) and configured to fit within the interior region 106 such that there is a minimum clearance between an interior annular wall 127 of the first elongate member 104 and the piston head 116. In other words, an inner diameter of the first elongate member 102 within the interior region 106 can be slightly larger than an outer diameter of the piston head 116 such that the piston head 116 can move back and forth within the interior region 106. In such an embodiment, the fluid may not easily flow past the piston head 116 to an area behind the piston head 116. In some embodiments, the piston head 116 may be sized and configured to have a greater clearance to the inner annular wall 127 of the first elongate member 102 such that fluid can more easily flow around the piston head 116 and contact a backside of the piston head 116 and the first portion 110 of the second elongate member 104. In such an embodiment, the fluid can exert a pressure on both sides of the piston head 116 and the first portion 110 of the second elongate member 104 disposed within the interior region 106. In addition, in some embodiments, the piston head 116 can include a plurality of apertures that allow for fluid communication.

In some embodiments, the medical device 100 can have a desirable compressability. The compressability can be controlled by fluids and/or gases within the device 100, as well as by materials of the medical device (e.g., elastomeric materials). In some embodiments, the compressability can be controlled by one or more apertures within the device that provide for removal and fluid communication of gases or fluids.

In another example, the movement of the first elongate member 102 and the second elongate member 104 relative to each other can be controlled by changing the viscosity of the fluid. For example, if a greater viscosity fluid is disposed within the interior region 106, the amount of force needed to move the second elongate member 104 relative to the first elongate member 102 may be greater than when a lower viscosity fluid is used. The viscosity of the fluid within the interior region 106 can also affect the ability of the fluid to flow past the piston head 116 (as in the example described above). For example, the greater the viscosity of the fluid, the greater clearance that may be needed between the piston head 116 and the interior annular wall 127 for the fluid to flow around the piston head 116.

The length of the medical device 100 can be adjusted while coupled within a patient's body one or multiple times, as needed as the patient's body changes (e.g., grows). For example, the medical device 100 can be coupled within the patient's body with the first elongate member 102 and the second elongate member 104 having a first length (as described above) and as the patient's body changes or grows, the first elongate member 102 and the second elongate member 104 can move relative to each other and have a second length (as described above). The medical device 100 may maintain the second length for a time period, and if the patient's body changes or grows again, the first elongate member 102 and the second elongate member 104 can move relative to each other again as described above.

Figure 5:
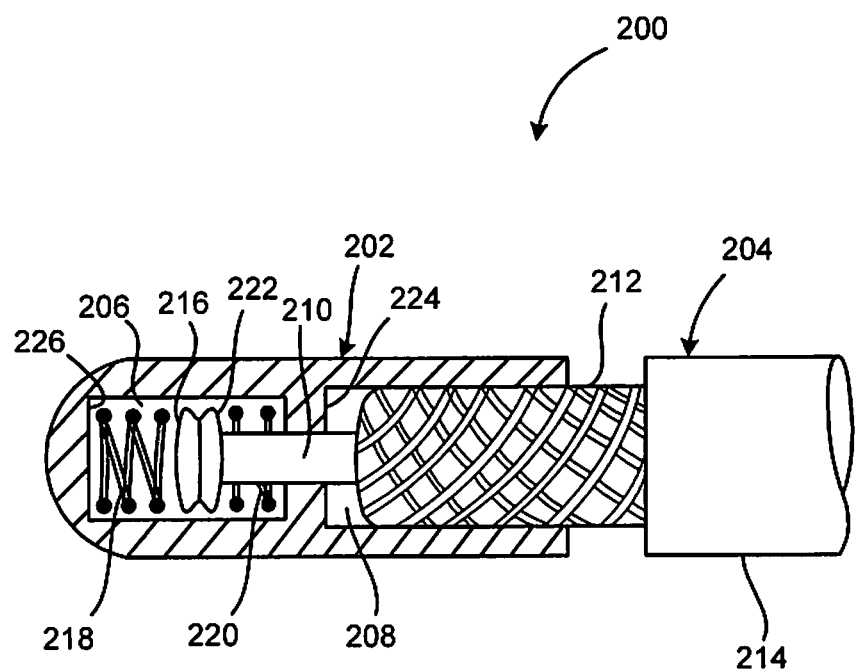
FIG. 5 is a side view partially in cross-section of a portion of a medical device according to another of the invention.

FIG. 5 illustrates an alternative embodiment of a medical device 200 that can be configured the same as, or similar to, and function the same as or similar to, the medical device 100. The medical device 200 includes a first elongate member 202 and a second elongate member 204 movably disposed within an interior region 206 of the first elongate member 202. The first elongate member 202 and the second elongate member 204 can each be coupled to an anatomical structure (e.g., a vertebra) within a patient's body via a support member (not shown) as mentioned above.

The first elongate member 202 defines a first interior region 206 and a second interior region 208 separated by an annular wall 224 that defines an opening in fluid communication with the first interior region 206 and the second interior region 208. The first elongate member 202 can be coupled to a first anatomical structure (e.g., a first vertebra) via a support member as described above for medical device 100. The second elongate member 204 includes a first portion 210, a second portion 212 and a third portion 214. The first portion 210 is movably disposed within the first interior region 206 and the second interior region 208 and extends through the opening defined in the annular wall 224 and can move back and forth within the first interior region 206 and the second interior region 208 as described above for medical device 100. At least a portion of the second portion 212 of the second elongate member 204 is movably disposed within the second interior region 208. The third portion 214 of the second elongate member 204 can be coupled to a second anatomical structure via a support member (not shown). The second portion 212 of the second elongate member 204 can be formed with a flexible material such that it can provide flexible movement of at least a portion of the second elongate member 204 relative to the first elongate member 202 as described above for the second portion 112 of medical device 100.

In this embodiment, a pair of springs 218 and 220 or other elastomeric materials are disposed within the interior region 206 and used to delay the elongation of the medical device 200. For example, the spring 218 can exert a force on a piston head 216 of the second elongate member 204, and the spring 220 can exert a force on a back side 222 of the piston head 216. Springs 218 and 220 can be configured to bias the piston head 216 to a desired position within the interior region 206. The greater the force needed to move or compress the spring 218 and the spring 220, the greater the force needed to move the first elongate member 202 and the second elongate member 204 relative to each other. In some embodiments, only a single spring can be used. For example, in some embodiments, only the spring 220 may be used. In such an embodiment, the spring 220 may bias the piston head 216 toward an end wall 226 of the first elongate member 202 and a predetermined force (e.g., based on the spring parameters) may be needed to compress the spring 222 and allow the first elongate member 202 and the second elongate member 204 to move relative to each other. The rate of delay can also be changed by using a spring or springs with different spring parameters (e.g., spring constant) and/or different types of spring (e.g., compression, extension).

Figure 6:
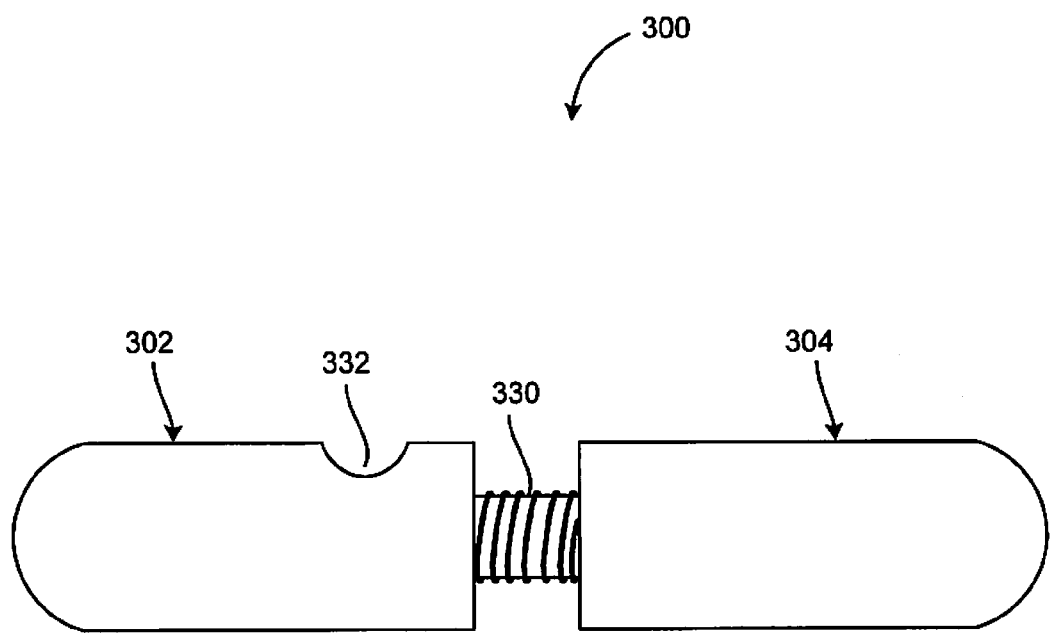
FIG. 6 is a side view of a medical device according to another embodiment of the invention.
Figure 7:
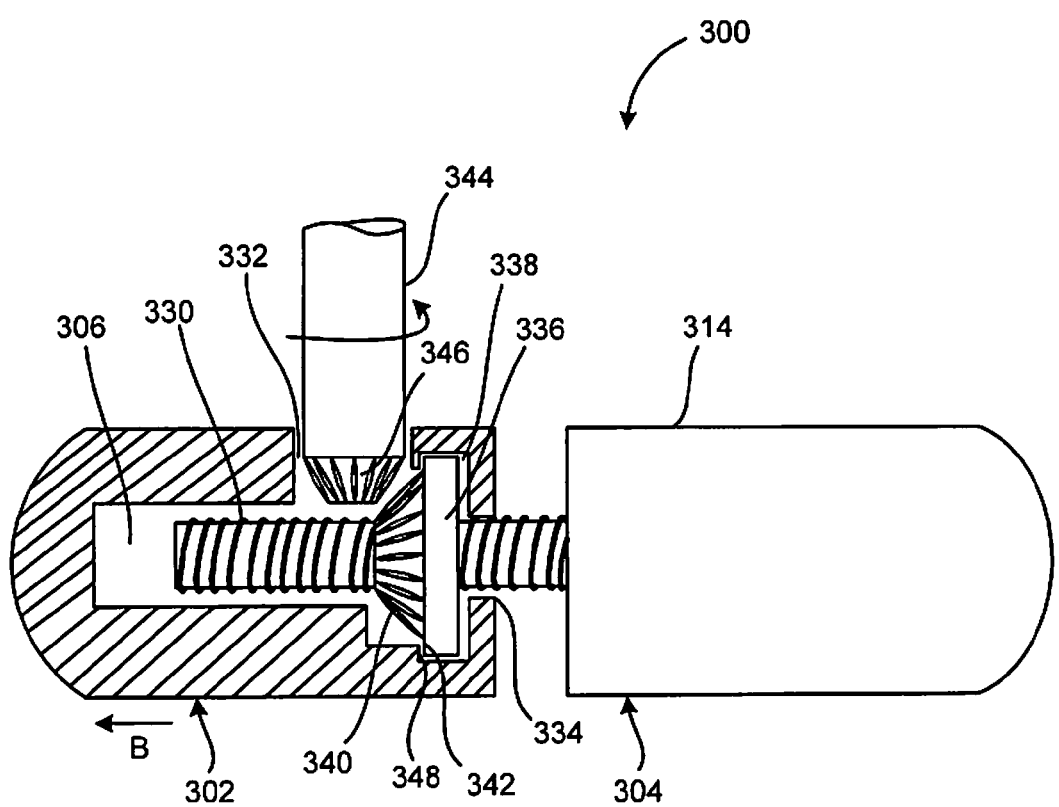
FIG. 7 is a partial cross-sectional side view of the medical device of FIG. 6.
Figure 8:
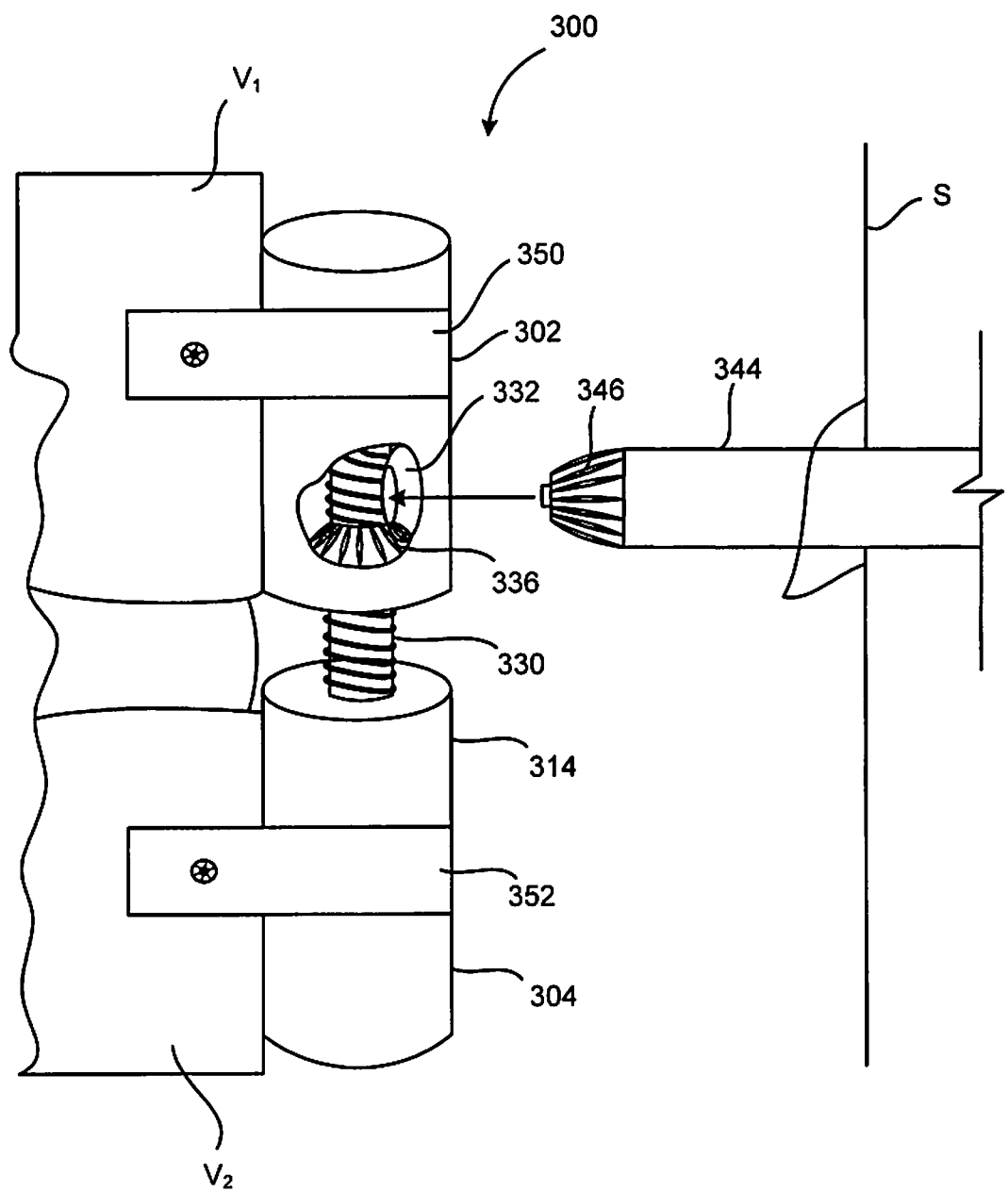
FIG. 8 is a perspective view of the medical device of FIG. 6 shown having a cut-away transparent portion and coupled to a first and second anatomical structure and a driver tool that can be used to actuate the medical device.

FIGS. 6-8 illustrate another embodiment of an adjustable medical device 300. The medical device 300 includes a first elongate member 302 and a second elongate member 304 each of which can be coupled to an anatomical structure within a patient's body via a support member as mentioned above. For example, the first elongate member 302 can be coupled to a support member 350 that is anchored to, or otherwise coupled to a first vertebra V1 within a spine of a patient, and the second elongate member 304 can be coupled to a second vertebra V2 via a support member 352, as shown in FIG. 8.

As shown in FIG. 7, the first elongate member 302 defines an interior region 306 and an opening 332 in an outer side wall of the first elongate member 302 and in fluid communication with the interior region 306. The first elongate member 302 also defines an opening 334 through which a portion of the second elongate member 304 can be received. An adjustment member 336 is rotatably received within an annular groove 338 within the interior region 306 of the first elongate member 302. The adjustment member 336 includes a threaded bevel gear portion 340 and an annular flange 342.

The second elongate member 304 includes a threaded first portion 330 and a second portion 314. The first portion 330 can be received through the opening 334 in the first elongate member 302 as shown in FIG. 7. The threaded first portion 330 also threadably extends through a mating threaded opening (not shown) in the bevel gear member 336. The threaded first portion 330 helps support and maintain a position of the adjustment member 336 within the annular groove 338. For example, the threaded first portion 330 can maintain the adjustment member 336 centered within the groove 338 such that the adjustment member 336 can rotate relative to the threaded first portion 330 within the groove 338. The second portion 314 can be coupled to an anatomical structure as discussed above for previous embodiments.

The first elongate member 302 and the second elongate member 304 collectively define a length of the medical device 300. The length of the medical device 300 can be adjusted before or after implantation within a patient's body to accommodate different uses and different distances between the anatomical structures to which the medical device 300 is coupled. The medical device 300 can have a first length when initially implanted within a patient, and can be adjusted to a second length different than the first length while implanted within the patient. For example, the length of the medical device 300 can be adjusted percutaneously.

In this embodiment, to adjust or change the length of the medical device 300, the adjustment member 336 can be rotated within the annular groove 338 such that the threaded opening of the adjustment member 336 threadably engages the threaded first portion 330 of the second elongate member 304 and causes the adjustment member 336 to move along the threaded first portion 330. For example, a driver tool 344 having a bevel gear tip portion 346 can engage the bevel gear portion 340 of the adjustment member 336 and can be turned or rotated to actuate or rotate the adjustment member 336. Advantageously, the driver tool 344 can be inserted percutaneously or minimally invasively to minimize trauma to a patient. As the adjustment member 336 rotates and engages the threaded first portion 330 of the second elongate member 304, the adjustment member 336 will move along the threaded first portion 330 along a longitudinal axis A-A defined by the second elongate member 304.

When the adjustment member 336 is rotated such that the adjustment member 336 is moved along the threaded first portion 330 in a direction of arrow B (shown in FIG. 7), the annular flange 342 of the adjustment member 336 will push or exert a force on an annular flange 348 within the interior region 306 of the first elongate member 302. This in turn will cause the first elongate member 302 to move relative to the second elongate member 304 in the direction of arrow B. In other words, a larger (e.g., longer) portion of the threaded first portion 330 of the second elongate member 304 will extend or telescope out of the interior region 306 of the first elongate member 302, resulting in a greater overall length of the medical device 300. As shown in FIG. 8, after the medical device 300 has been implanted in a patient, the driver tool 344 can be inserted through an opening in the skin S of the patient to percutaneously adjust the length of the medical device 300 as needed.

In alternative embodiments, the adjustment member 336 can be disposed outside of the interior region 306 of the first elongate member 302. For example, the adjustment member 336 can be coupled to the first elongate member 302 such that as the adjustment member 336 is rotated it can exert a force on the first elongate member 302 and cause the first elongate member 302 to move relative to the second elongate member 304. In some embodiments, the adjustment member 336 can be disposed at least partially within a separate adjustment member housing (not shown) that is coupled to or couplable to the first elongate member 302. The adjustment member housing can define an opening to receive the driver tool 344 to actuate the adjustment member 336 as described above.

In some embodiments, the medical device 300 can include a cover member (not shown) disposed over the opening 332 in the first elongate member 302. The cover member can be configured to allow a tool, such as the driver tool 344, to be inserted through the cover member to engage the bevel gear member 336 as described above. The cover member can prevent or limit bodily material from passing through the opening 332 when the medical device 300 is implanted within a patient. The cover member can be, for example, a membrane having a closable opening that can allow the tool 344 to pass through and that can reseal itself after the tool is removed. In some embodiments, the cover member can be a one-way valve.

Figure 9:
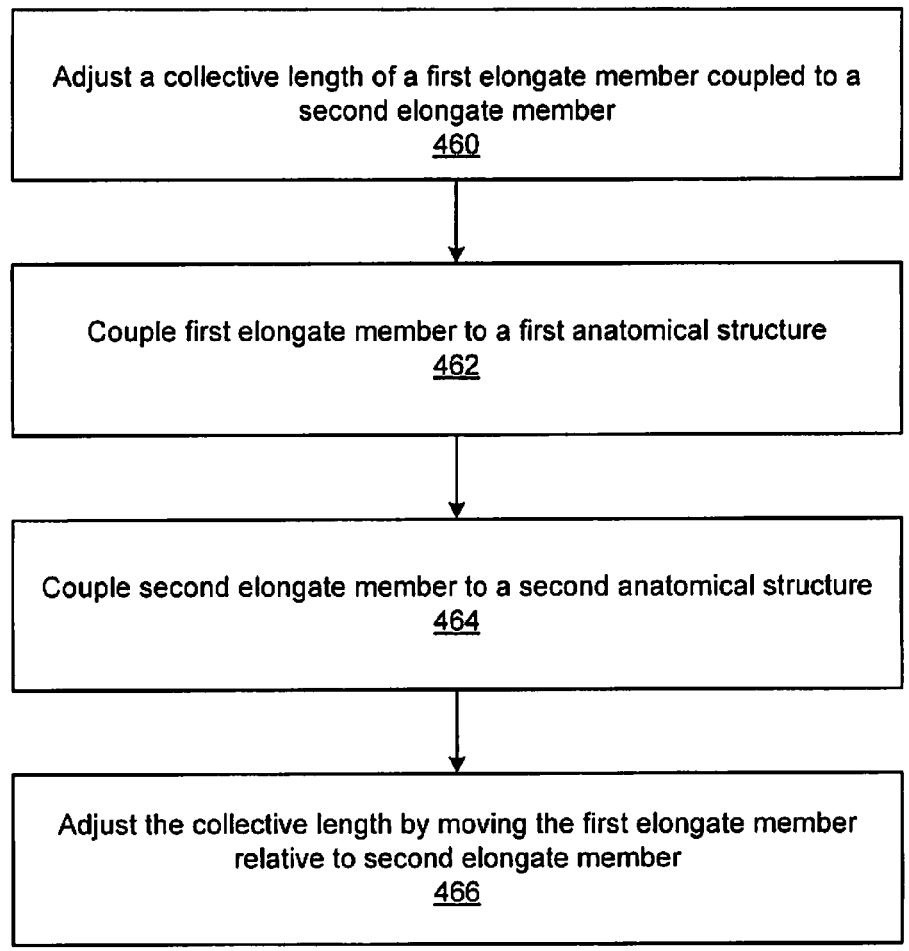
FIG. 9 is a flowchart illustrating a method of adjusting a length of a medical device, according to an embodiment.

FIG. 9 is a flowchart of a method of adjusting the length of a medical device (e.g., 300) according to an embodiment. As shown in FIG. 9, the method includes at 460 adjusting a collective length of a first elongate member (e.g., 302) of the medical device coupled to a second elongate member (e.g., 304) of the medical device. For example, prior to implanting the medical device within a patient's body, the length can be adjusted to accommodate the length needed for the particular anatomical structure for that particular patient. At 462, the first elongate member of the medical device can be coupled to a first anatomical structure within a body of a patient, and at 464 the second elongate member can be coupled to a second anatomical structure within the body of the patient. In some embodiments, the first anatomical structure and the second anatomical structure are a first vertebra and a second vertebra, respectively. At least a portion of the second elongate member is movably disposed within an interior region of the first elongate member. The first elongate member and the second elongate member have a first length when the first elongate member is coupled to the first anatomical structure and the second elongate member is coupled to the second anatomical structure (e.g., the length adjusted at 460). At 466, after coupling the first elongate member and the second elongate member to the first and second anatomical structures, respectively, the collective length of the first elongate member and the second elongate member can be adjusted by moving the first elongate member relative to the second elongate member such that the first elongate member and the second elongate member collectively have a second length different than the first length. For example, to move the first elongate member relative to the second elongate member an adjustment member (e.g., adjustment member 336) coupled to the first elongate member can be rotatably actuated. The first elongate member can be moved relative to the second elongate member percutaneously. In some embodiments, the second length is greater than the first length.

The various components of the medical devices (e.g., 100, 200, 300) described herein can be formed with any biocompatible material used for such medical devices. For example, each of the various components can be formed with one or more biocompatible plastics and/or one or more biocompatible metals, such as, for example, titanium and stainless steel. Other suitable materials can be PEEK, chromium, PCU, PET and various combinations thereof.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments. It should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A medical device, comprising:
a first elongate member defining a first interior region and a second interior region separated by a fixed annular wall, the first elongate member configured to be coupled to a first anatomical structure within a body of a patient; and
a second elongate member configured to be coupled to a second anatomical structure within the body of the patient, wherein the second elongate member comprises a flexible portion disposed in the second interior region of the first elongate member but not the first interior region of the first elongate member, wherein the first interior region is enclosed to retain a portion of the second elongate member,
the first elongate member and the second elongate member collectively having a first configuration in which the first elongate member and the second elongate member collectively have a first length when the second elongate member is disposed within the first elongate member,
wherein when the first elongate member is coupled to the first anatomical structure and the second elongate member is coupled to the second anatomical structure, the first elongate member and the second elongate member can he moved from the first configuration to a second configuration in which the first elongate member and the second elongate member collectively have a second length different than the first length.

2. The medical device of claim 1, wherein the first anatomical structure is a first vertebra and the second anatomical structure is a second vertebra.

3. The medical device of claim 1, wherein the second length is greater than the first length.

4. The medical device of claim 1, wherein the flexible portion is configured to allow a portion of the second elongate member to bend relative to a longitudinal axis defined by the first elongate member.

5. The medical device of claim 1, further comprising:
a volume of fluid disposed within the first interior region of the first elongate member, the volume of fluid configured to at least partially control the movement of the first elongate member and the second elongate member between the first configuration and the second configuration.

6. The medical device of claim 1, further comprising:
a spring member disposed within the first elongate member, the spring member configured to at least partially control the movement of the first elongate member and the second elongate member between the first configuration and the second configuration.

7. The medical device of claim 1, wherein the second elongate member includes a first portion, a second portion, and a third portion, wherein the second portion is positioned between the first portion and the third portion, and the second portion is the flexible portion.

8. The medical device of claim 7, wherein the annular wall defines an opening in fluid communication between the first interior region and the second interior region, wherein the first portion of the second elongate member is movably disposed within the first interior region and the second interior region and extends through the opening in the annular wall.

9. The medical device of claim 7, wherein the first portion of the second elongate member can slidably move along a longitudinal axis defined by the first elongate member and within the first interior region of the first elongate member.

10. The medical device of claim 7, wherein the first portion of the second elongate member has a free-end positioned within the interior region of the first elongate member.

11. The medical device of claim 7, wherein the first portion of the second elongate member includes a shaft and a piston head sized and configured to fit within the first interior region.

12. The medical device of claim 7, wherein the flexible material is configured to provide flexible movement such that the third portion is capable of being disposed at different angles relative to a longitudinal axis defined by the first elongate member.

13. The medical device of claim 7, wherein the third portion of the second elongate member is configured to be coupled to the second anatomical structure within the body of the patient.

14. A medical device, comprising:
a first elongate member defining a first interior region and a second interior region separated by a fixed annular wall, the first elongate member configured to be coupled to a first anatomical structure within a body of a patient; and
a second elongate member configured to be coupled to a second anatomical structure within the body of the patient, wherein the second elongate member comprises a flexible portion disposed in the second interior region of the first elongate member but not the first interior region of the first elongate member, wherein the first interior region is enclosed to retain a portion of the second elongate member, the first elongate member and the second elongate member collectively having a first length when the first elongate member is coupled to the first anatomical structure and the second elongate member is coupled to the second anatomical structure, at least one of the first elongate member or the second elongate member configured to move relative to the other when a force is exerted by at least one of the first anatomical structure on the first elongate member or the second anatomical structure on the second elongate member such that the first elongate member and the second elongate member collectively have a second length different than the first length.

15. The medical device of claim 14, wherein the second length is greater than the first length.

16. The medical device of claim 14 wherein the first anatomical structure is a first vertebra and the second anatomical structure is a second vertebra.

17. The medical device of claim 14, wherein the flexible portion is configured to allow a portion of the second elongate member to bend relative to a longitudinal axis defined by the first elongate member.

18. The medical device of claim 14, further comprising:
a volume of fluid disposed within the first interior region defined by the first elongate member, the volume of fluid configured to at least partially control the movement of the first elongate member and the second elongate member relative to each other.

19. The medical device of claim 14, further comprising:
a spring member disposed within the first elongate member, the spring member configured to at least partially control the movement of the first elongate member and the second elongate member relative to each other.

* * * * *